US012806065B2

(12) United States Patent
Dai et al.

(10) Patent No.: US 12,806,065 B2
(45) Date of Patent: Nov. 24, 2026

(54) MOLD FOR MOLDING POLYURETHANE CONDOM, AND PREPARATION METHOD AND USE METHOD FOR MOLD

(71) Applicant: RECKITT BENCKISER HEALTH LIMITED, Berkshire (GB)

(72) Inventors: Jiabing Dai, Lanzhou (CN); Weihu Li, Suzhou (CN); Linlin Feng, Lanzhou (CN); Liang Chen, Lanzhou (CN)

(73) Assignee: Reckitt Benckiser Health Limited, Slough (GB)

( * ) Notice: Subject to any disclaimer, the term of this patent is extended or adjusted under 35 U.S.C. 154(b) by 468 days.

(21) Appl. No.: 17/916,110

(22) PCT Filed: Jun. 16, 2020

(86) PCT No.: PCT/CN2020/096323
§ 371 (c)(1),
(2) Date: Sep. 30, 2022

(87) PCT Pub. No.: WO2021/196413
PCT Pub. Date: Oct. 7, 2021

(65) Prior Publication Data

US 2023/0149206 A1 May 18, 2023

(30) Foreign Application Priority Data

Mar. 31, 2020 (CN) ......................... 202010242233.8
May 20, 2020 (CN) ......................... 202010430499.5
May 20, 2020 (CN) ......................... 202010431395.6

(51) Int. Cl.
*A61F 6/04* (2006.01)
*A61F 6/06* (2006.01)
(Continued)

(52) U.S. Cl.
CPC ................ *A61F 6/04* (2013.01); *A61F 6/065* (2013.01); *A61L 31/06* (2013.01); *A61L 31/10* (2013.01);
(Continued)

(58) Field of Classification Search
CPC .................................. A61F 6/04; A61F 6/065
See application file for complete search history.

(56) References Cited

U.S. PATENT DOCUMENTS 4,104,289 A * 8/1978 Jones ................ C08K 5/34924 428/407
4,567,221 A 1/1986 Maruyama et al.
(Continued)

FOREIGN PATENT DOCUMENTS

CN 101961279 A 2/2011
CN 102078233 A 6/2011
(Continued)

OTHER PUBLICATIONS

Machine translation of CN 202200457, retrieved from USPTO database Mar. 13, 2025 (Year: 2025).*
(Continued)

*Primary Examiner* — Timothy Kennedy
(74) *Attorney, Agent, or Firm* — Lerner David LLP

(57) ABSTRACT

The present disclosure provides a mold for molding a polyurethane condom, and methods for manufacturing and using the mold. The mold (200) has a surface roughness of 0.2 μm or less, is formed from a thermoplastic polymer having a surface tension of 10-35 mN/m. The mold (200) for molding a polyurethane condom is prepared by injection molding the thermoplastic polymer. When the mold (200) is used, the mold (200) is hung vertically and dipped in an emulsion containing a polyurethane resin to obtain a dipped mold (200), then the dipped mold (200) is removed and
(Continued)

dried to form a polyurethane film on its surface, and then demolded to obtain a polyurethane condom (100). The condom formed by the mold (200) is thin and has excellent flexibility and strength, satisfying the market demand for the product.

19 Claims, 2 Drawing Sheets

(51) Int. Cl.

| | |
|---|---|
| ***A61L 31/06*** | (2006.01) |
| ***A61L 31/10*** | (2006.01) |
| ***A61L 31/14*** | (2006.01) |
| ***B29C 33/40*** | (2006.01) |
| ***B29C 41/14*** | (2006.01) |
| ***B29C 41/40*** | (2006.01) |
| ***C09J 175/04*** | (2006.01) |
| *B29C 41/22* | (2006.01) |
| *B29K 75/00* | (2006.01) |
| *B29K 105/00* | (2006.01) |
| *B29L 31/00* | (2006.01) |

(52) U.S. Cl.

CPC .............. *A61L 31/14* (2013.01); *B29C 33/40* (2013.01); *B29C 41/14* (2013.01); *B29C 41/40* (2013.01); *C09J 175/04* (2013.01); *A61F 2006/043* (2013.01); *A61L 2420/02* (2013.01); *A61L 2420/04* (2013.01); *A61L 2420/08* (2013.01); *B29C 41/22* (2013.01); *B29K 2075/00* (2013.01); *B29K 2105/0097* (2013.01); *B29L 2031/7538* (2013.01)

(56) References Cited

U.S. PATENT DOCUMENTS

| | | | | |
|---|---|---|---|---|
| 4,660,228 | A | 4/1987 | Ogawa et al. | |
| 4,941,938 | A | 7/1990 | Karlsson | |
| 5,314,653 | A | 5/1994 | Haralambopoulos | |
| 5,342,291 | A | 8/1994 | Scholz et al. | |
| 5,458,936 | A * | 10/1995 | Miller .................. | C08G 18/664 128/918 |
| 5,571,567 | A | 11/1996 | Shah | |
| 5,595,704 | A * | 1/1997 | Hayashi .................. | B29C 41/14 425/269 |
| 6,020,070 | A | 2/2000 | Hoerner et al. | |
| 8,623,169 | B2 | 1/2014 | Delfino et al. | |
| 9,173,767 | B2 | 11/2015 | Hill et al. | |
| 2004/0163652 | A1 | 8/2004 | Watson | |
| 2004/0194786 | A1 | 10/2004 | Manning | |
| 2005/0066414 | A1 | 3/2005 | Yu et al. | |
| 2010/0229873 | A1 | 9/2010 | Hill et al. | |
| 2012/0181726 | A1 | 7/2012 | Platt et al. | |
| 2019/0022898 | A1 | 1/2019 | Janssen et al. | |
| 2023/0088356 | A1* | 3/2023 | Kodemura .............. | C08L 13/02 264/301 |

FOREIGN PATENT DOCUMENTS

| | | | | |
|---|---|---|---|---|
| CN | 102107473 | A | 6/2011 | |
| CN | 202200457 | U | 4/2012 | |
| CN | 202754933 | U | 2/2013 | |
| CN | 103692733 | A | 4/2014 | |
| CN | 104339485 | A | 2/2015 | |
| CN | 205255363 | U | 5/2016 | |
| CN | 106273142 | A | 1/2017 | |
| CN | 107057129 | A | 8/2017 | |
| CN | 107266645 | A | 10/2017 | |
| CN | 107383590 | A | 11/2017 | |
| CN | 107411871 | A | 12/2017 | |
| CN | 109160990 | A | 1/2019 | |
| CN | 110027153 | A | 7/2019 | |
| CN | 111072902 | A | 4/2020 | |
| CN | 111658288 | A | 9/2020 | |
| CN | 111748110 | A | 10/2020 | |
| EP | 3479985 | A2 | 5/2019 | |
| GB | 2252528 | A | 8/1992 | |
| JP | S50-14755 | A | 2/1975 | |
| JP | H02-4502 | A | 1/1990 | |
| JP | H0780017 | A | 3/1995 | |
| JP | 2000280268 | A | 10/2000 | |
| JP | 2000342616 | A | 12/2000 | |
| JP | 2009012307 | A | 1/2009 | |
| KR | 19980034853 | A | 8/1998 | |
| KR | 20070110996 | A | 11/2007 | |
| WO | WO-9514447 | A1 * | 6/1995 | ............... A61F 6/04 |
| WO | 2010095665 | A1 | 8/2010 | |
| WO | 2016026256 | A1 | 2/2016 | |
| WO | 2016188328 | A1 | 12/2016 | |

OTHER PUBLICATIONS

Alpa, https://www.alpapowder.com/112971/, Mar. 11, 2021 (Year: 2021).*

Calcium City, https://www.calciumcity.com/what-is-the-difference-between-heavy-calcium-and-light-calcium-in-plastics-.html , Feb. 15, 2022 (Year: 2022).*

JetMills, https://www.jet-mills.com/the-difference-between-heavy-calcium-and-light-calcium-in-polymer-applications/ , Aug. 13, 2024 (Year: 2024).*

Vtalc, https://www.vtalc.com/news/understanding-calcium-carbonate-comprehensive-analysis-of-17-differences-between-light-calcium-and-heavy-calcium , Sep. 2, 2025 (Year: 2025).*

Inno Tape, https://www.innotape.de/en/blog/surface-energy#:~:text=Low%2Denergy%20surfaces%2C%20on%20the,31%20mN/m%2C%20respectively. , retrieved Jan. 9, 2026 (Year: 2026).*

Oreworld, https://www.csacement.com/the-difference-between-heavy-and-light-calcium-carbonate.html, retrieved Jan. 9, 2026 (Year: 2026).*

International Search Report and Written Opinion received in corresponding PCT Application No. PCT/CN2020/096323 mailed Jan. 4, 2021 with English translation (12 pages total).

Extended European Search Report dated Mar. 15, 2024 in EP App No. 20928950.3, filed Jun. 16, 2020.

Notification of Reason for Rejection dated Mar. 21, 2024, in JP Application No. 2022-559542, filed Jun. 16, 2020.

Office Action dated Jun. 12, 2025, in Chinese App No. CN202080099083.8, filed Mar. 10, 2011.

Office Action dated Sep. 13, 2024 in CN Application No. 202210689196.4, filed May 20, 2020.

Extended European Search Report dated Apr. 16, 2024 in EP .Application No. 20928974.3; filed Oct. 22, 2020.

International Search Report and Written Opinion received in corresponding PCT Application No. PCT/CN2020/122617 mailed Jan. 20, 2021 with English translation (13 pages total).

Search Report dated Dec. 30, 2025 from the Office Action for Chinese Application No. 202080099166.7 issued Jan. 1, 2026, pp. 1-3.

* cited by examiner

MOLD FOR MOLDING POLYURETHANE CONDOM, AND PREPARATION METHOD AND USE METHOD FOR MOLD

CROSS-REFERENCE TO RELATED APPLICATIONS

This application is a U.S. National Phase of International Patent Application No. PCT/CN2020/096323, filed on 16 Jun. 2020, which claims priority to CN application No. 202010242233.8 filed 31 Mar. 2020, CN application No. 202010430499.5 filed 20 May 2020, and CN application No. 202010431395.6 filed 20 May 2020. The entire contents of these applications are incorporated herein by reference in their entirety.

TECHNICAL FIELD

The present disclosure relates to the field of condom materials, and in particular, to a mold for molding a polyurethane condom, a method for manufacturing the mold, and a method for using the mold.

BACKGROUND

Condoms are simple devices widely used in the world for contraception and prevention of sexually transmitted diseases. The current condom products mainly include natural rubber latex condoms and polyurethane condoms.

In the dip molding process for a natural latex rubber condom, a mold made of glass or a metal material such as stainless steel is mainly used. Since the natural latex rubber material has a surface tension close to that of glass and stainless steel, the film formed from natural latex rubber on the surfaces of these two materials shows relatively weak adhesion. Furthermore, natural latex rubber has a swelling property in an alkaline environment. Therefore, natural latex rubber condoms are demolded by swelling in ammonia water after being molded on the surface of a glass mold or a metal mold.

However, a condom made of a polyurethane material does not have the swelling property of natural latex rubber, and has a surface tension of about 55 mN/m. A dried coating film thereof has a surface tension of about 45 mN/m. A polyurethane emulsion can be spread on molds of glass, ceramic, and stainless steel, and a dried waterborne polyurethane film has very strong adhesion to these molds, causing difficulty in rolling and demolding, preventing these two materials from being directly used for dip molding of polyurethane condoms. In order to solve the problem in molding of polyurethane, two methods are currently used in the world: (1)alkylating the glass surface to bring the surface tension of the glass close to that of a polyurethane material, whereby the problem with film formation and demolding of polyurethane materials on glass can be solved, but the time period available for effective use after alkylation is as short as about 30 h, not allowing continuous production; and the stability of quality of the polyurethane condom products cannot be effectively guaranteed in the production process because the effect of alkylation varies from time to time; and (2) Precoating the surface of glass or stainless steel with a layer of a release agent, whereby the problem with continuous production can be solved, but the release agent may be carried into the condom material during the production process, posing a potential risk to the performance and biosafety of the product.

Therefore, there is a need for further improvement and optimization of the mold for molding of polyurethane condoms, which also represents a research hotspot and difficulty in this field.

SUMMARY OF THE INVENTION

The present invention is made in view of the above-described drawbacks in the prior art. One of the objectives of the present disclosure is to provide a mold for molding a polyurethane condom, and the polyurethane condom is thin and has excellent flexibility and strength, satisfying the market demand for the product.

Another objective of the present disclosure is to provide a method for manufacturing the mold for molding a polyurethane condom.

Another objective of the present disclosure is to provide a method for using the mold for molding a polyurethane condom.

The present disclosure provides a mold for molding a polyurethane condom, which has a surface roughness of 0.2 μm or less, and is composed of a thermoplastic polymer having a surface tension of 10-35 mN/m.

In one embodiment, the thermoplastic polymer is any one selected from polyurethane, polymethyl methacrylate, polystyrene, polyethylene, polyvinyl chloride, polypropylene, polystyrene, acrylonitrile-butadiene-styrene, polyamide, polycarbonate, polyoxymethylene, modified polyphenylene oxide, thermoplastic polyester, polyimide, polyphenylene sulfide, polysulfones, aromatic polyamides, polyarylate, polyphenyl ester, polyaryletherketone, a liquid crystalline polymer, fluororesin, and materials obtained by organic modification of the above polymers or by inorganic modification by filling the above polymers with an inorganic material, or any combination thereof.

In an embodiment, the organic modification is any one selected from organosilicon modification, organofluorine modification, silane modification, acrylate copolymerization modification, vinyl monomer modification, and aromatic monomer modification, or any combination thereof.

In an embodiment, the inorganic modification is any one selected from heavy calcium modification, talc modification, graphene modification, water glass modification, attapulgite modification, kaolin modification, light calcium modification, and glass microbeads modification, and any combination thereof.

In one embodiment, the polyurethane condom is a male condom, and the mold comprising: a head portion, and a tail portion connected to the head portion, wherein the head portion has a columnar shape with a gradually increasing diameter, and has a slope greater than 0° and less than or equal to 5°.

In one embodiment, the head portion has a front end provided with a semen pouch.

In one embodiment, the head portion has a length of 200-260 mm.

In one embodiment, the head portion is connected to the tail portion via a transition section.

In one embodiment, the tail portion has a columnar shape with a constant diameter.

In one embodiment, the tail portion has a columnar shape with a gradually increasing diameter, and has a slope greater than 0° and less than or equal to 3°.

In one embodiment, the polyurethane condom is a female condom.

In one embodiment, the polyurethane condom is a heterotypic condom, and the mold has a surface provided with floating points or screw threads.

In one embodiment, the mold has a thickness of 2-10 mm, or is a solid mold.

In one embodiment, when the mold is placed vertically, the mold has an angle less than 5° with respect to the vertical line.

The present disclosure also provides a method for manufacturing a mold for molding a polyurethane condom, comprising the steps of:

providing a thermoplastic polymer having a surface tension of 10-30 mN/m;

injection molding the thermoplastic polymer to produce a mold for molding a polyurethane condom;

wherein the mold has a surface roughness of 0.2 μm or less.

In one embodiment, the injection molding is carried out by three-shot feed and two-stage injection molding.

The present disclosure also provides a method for using a mold for molding a polyurethane condom, comprising the steps of:

providing a mold;

providing an emulsion comprising a polyurethane resin;

hanging the mold vertically and dipping it in the emulsion containing the polyurethane resin to obtain an dipped mold;

removing the dipped mold and drying it to form a polyurethane film on the surface of the mold;

demolding;

wherein the mold has a surface roughness of 0.2 μm or less, and is composed of a thermoplastic polymer having a surface tension of 10-35 mN/m.

In one embodiment, the polyurethane condom has a 100% tensile modulus of 2.5 N/mm$^2$ or lower.

In one embodiment, the polyurethane condom has a burst pressure of 1 kPa or more, a burst volume of 5 L or more, and a 100% modulus of 3.5 N/mm$^2$ or lower.

The polyurethane condom having an adhesive layer provided according to the present disclosure is prepared by using a mold for molding the polyurethane condom, wherein the mold is composed of a thermoplastic polymer having a surface tension of 10-35 mN/m, so that the polyurethane can uniformly form a film directly on the surface of the mold by dip molding. A film formed therefrom after drying has weak adhesion, allowing uniform demolding without the aid of a release agent, which ensures the uniformity of the polyurethane film and avoids introduction of other substances, thereby sufficiently ensuring the performance and biological safety of the polyurethane condom product. In addition, according to the mold provided in the present disclosure, the polyurethane material can be directly post-treated and shaped on the surface of the mold for raw material properties, without addition of other processes due to demolding, etc., which greatly simplifies the operation procedure, improves the production efficiency and increases the qualification rate of products. The raw materials for the mold of the present disclosure have a low cost and a rich source, and the molding process is simple, safe, and environmentally friendly. Other features, benefits, and advantages will be apparent from the disclosure detailed herein, including the description and claim.

BRIEF DESCRIPTION OF DRAWINGS

The drawings used in the embodiments will be briefly described below to more clearly describe the technical solutions in the embodiments of the present disclosure. It is to be understood that the following drawings depict only certain embodiments of the invention and are therefore not to be considered limiting its scope. For a person of ordinary skill in the art, other relevant drawings can also be obtained according to these drawings without paying any inventive effort.

DETAILED DESCRIPTION OF THE INVENTION

Figure 1:
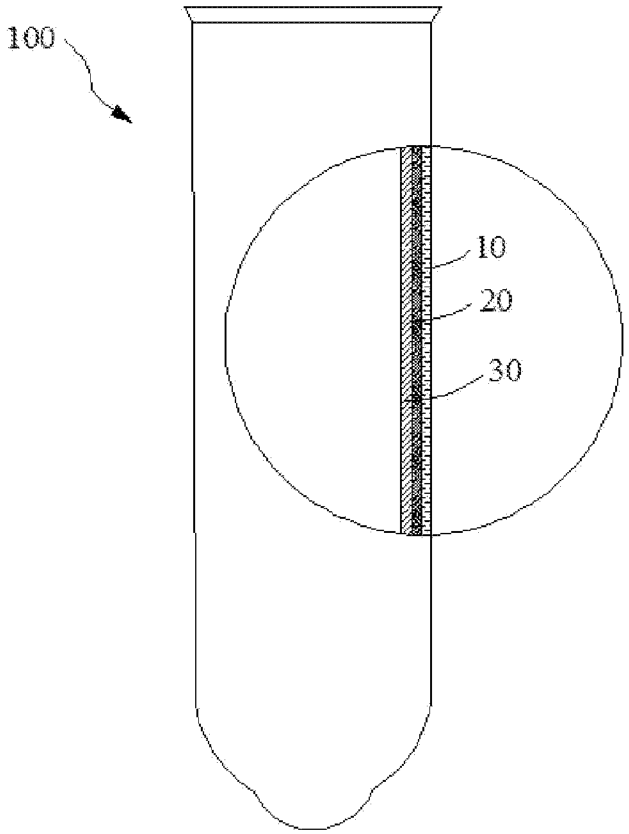
FIG. 1 illustrates a schematic structure of the polyurethane condom according to one specific embodiment of the present disclosure.

The technical solutions of the embodiments in the present disclosure will be clearly and fully described with reference to the accompanying drawings, in order to provide a clear understanding of for the objectives, technical solutions and advantages of the embodiments of the present disclosure. Obviously, it is to be understood that the described embodiments are part of, and not all of, the present disclosure. The components of the embodiments in the present disclosure, which are generally described and illustrated in the drawings herein, can be configured and designed upon different needs.

Figure 2:
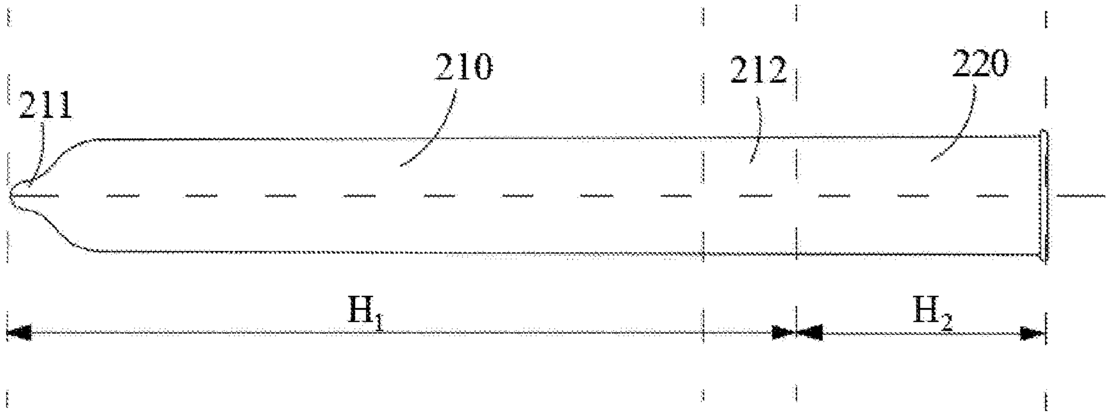
FIG. 2 illustrates a schematic structure of a mold for molding a polyurethane condom according to one specific embodiment of the present disclosure.
Figure 3:
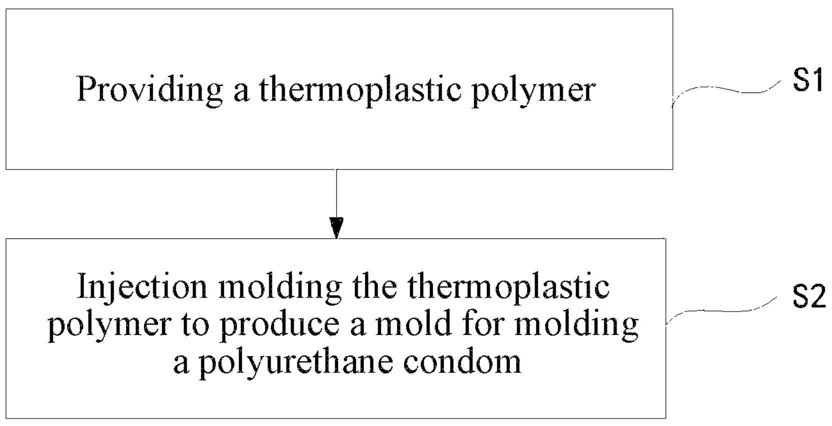
FIG. 3 illustrates a schematic flow diagram of a method for manufacturing the mold for molding a polyurethane condom according to one specific embodiment of the present application.

As shown in FIGS. 1-3, the process for preparing a polyurethane condom 100 includes performing molding on a mold 200. Specifically, the polyurethane condom 100 is prepared by molding the raw materials for the polyurethane condom 100, such an emulsion including a polyurethane resin, on a mold 200 by dip molding, and the polyurethane condom 100 has high strength, high compactness, and good biocompatibility, may have a thickness of, for example, 0.001 mm to 0.08 mm, preferably 0.05 mm to 0.04 mm, such as 0.01 mm, 0.015 mm, 0.02 mm, and 0.030 mm, and can provide a user with a more comfortable experience, and a softer and more delicate skin feel, without the problem of allergy.

The polyurethane condom 100 having a thickness within the above range has a burst pressure of for example 1 kPa or more, preferably 3 kPa or more, for example, 3 kPa, 4 kPa, or 5 kPa, and a burst volume of for example 5 L or more, for example, 6 L, 8 L, or 10 L.

The polyurethane condom 100 may have a strength, e.g. tensile strength, of for example 30 MPa or more, preferably 70 MPa or more, and a 100% modulus of for example 3.5 N/mm$^2$ or lower, such as 2 N/mm$^2$, 1.8 N/mm$^2$, 1.5 N/mm$^2$, or 1 N/mm$^2$.

It is noteworthy that the emulsion comprising a polyurethane resin has a surface tension for example in a range of 20-80 mN/m, preferably in a range of 30-60 mN/m, such as 32 mN/m, 40 mN/m, 50 mN/m, 55 mN/m, and 58 mN/m. After being molded and dried on the surface of the mold 20 provided in the present disclosure, the polyurethane film has a surface tension in a range of 15-68 mN/m, such as 20 mN/m, 28 mN/m, 45 mN/m, or 50 mN/m. Within the above range, the emulsion containing the polyurethane resin may be uniformly spread on the mold 200, and the dried film has low adhesion, thereby ensuring uniform film formation and demolding.

In some embodiments, the emulsion comprising a polyurethane resin may form, for example, a layer from the emulsion of the polyurethane resin mixed with other auxiliary agents. The auxiliary agents may be, for example, functional auxiliary agents such as a lubricant, a bactericide, a thickener, a wetting agent, an antifoaming agent, water, and the like, but not limited thereto. The polyurethane resin may be any suitable kind of aliphatic polyurethane or aromatic polyurethane, and may be preferably, for example, an anionic, cationic, nonionic, amphoteric, solvent-based or solvent-free polyurethane. The raw materials and preparation process for the polyurethane may be adjusted to prepare a desired polyurethane. Furthermore, from the viewpoint of obtaining excellent film-forming and demolding properties, the polyurethane resin may be selected from, for example, a polyurethane resin synthesized from polyether/polyester polyols, may have a 100% tensile modulus of 3.5 $N/mm^2$ or lower, and a tensile strength of 25 MPa or more, for example. The present invention is certainly not limited thereto.

As shown in FIGS. 1 and 2, the present disclosure provides a specific embodiment of the polyurethane condom 100, which can have a multi-layer structure formed by multiple dip moldings on the mold 200, such as three layers (for example the first layer 10, the second layer 20, and the third layer 30), four layers, five layers, six layers, etc., but not limited thereto, as adjustable according to practical needs. Here, according to the types of the mold 200, the polyurethane condom 100 may be configured as a male condom, and it should be understood that the polyurethane condom 100 may also be configured as a female condom or other heterotypic condoms according to the types of the mold 200. For example, the mold 200 may be provided with floating points or screw threads, but not limited thereto.

The mold 200 is composed of a thermoplastic polymer having a surface tension in a range of 10-35 mN/m, for example, 25-35 mN/m, such as 35 mN/m, 32 mN/m, 30 mN/m, or 28 mN/m. When the surface tension of the thermoplastic polymer is less than 10 mN/m, it is difficult to spread the polyurethane emulsion uniformly on the mold 200 composed of the thermoplastic polymer; and when the surface tension of the thermoplastic polymer is more than 35 mN/m, the adhesion between a dried film formed from the polyurethane emulsion and the mold 200 composed of the thermoplastic polymer is too strong to allow smooth demolding. Within the above range, when the polyurethane emulsion is molded, for example, dip-molded, on the mold 200, the polyurethane emulsion can uniformly form a film directly on the surface of the mold, and a film formed after drying has low adhesion to allow uniform demolding without the aid of a release agent, which ensures uniformity of the polyurethane film and avoids introduction of other substances, thereby sufficiently ensuring the performance and biological safety of the polyurethane condom product.

In some embodiments, the thermoplastic polymer material may be, for example, ethylene-based polymers, propylene-based polymers, diene-based polymers, aromatic polymers, and polyurethanes, polycarbonates, polymethyl methacrylates, polyamides, thermoplastic polyesters, polyoxymethylenes, and halogenated thermoplastic polymers, such as thermoplastic polyesters.

In some embodiments, the ethylene-based polymer may specifically be polyethylene and copolymers thereof, ethylene-butene copolymers, ethylene-hexene copolymers, ethylene-octene copolymers, ethylene-propylene-butene copolymers, ethylene-vinyl acetate copolymers, ethylene-ethyl acrylate copolymers, ethylene-methyl methacrylate copolymers, chlorinated polyethylene, ethylene-vinyl alcohol copolymers, or the like.

The propylene-based polymer may be polypropylene, polyacrylonitrile, propylene-ethylene copolymers, propylene-butene copolymers, propylene-hexene copolymers, propylene-octene copolymers, or the like.

The diene-based polymer may be polybutadiene, polyisoprene, butadiene-styrene copolymers, butadiene-acrylonitrile copolymers, ethylene-propylene-5-ethylene-2-norbornene copolymers, ethylene-propylene-dicyclopentadiene copolymers, or ethylene-propylene-5-vinyl-2-norbornene copolymers.

The aromatic polymers may be polystyrene, modified polyphenylene ether, or copolymers thereof, such as styrene-acrylonitrile copolymers, styrene-acrylonitrile-butadiene copolymers, acrylic rubber-acrylonitrile-styrene copolymers, or acrylonitrile-chlorinated polyethylene-styrene copolymers.

The above mentioned materials may be further selected from, for example, waterborne polyurethane, polymethyl methacrylate, polystyrene, polyethylene, polyvinyl chloride, polypropylene, polystyrene, butadiene-styrene, polyamide (e.g. polyamide 6, polyamide 11, polyamide 12, polyamide 6.6, polyamide 4.6, polyamide 6.10, and polyamide 6.12, etc.), polycarbonate, polyoxymethylene, modified polyphenylene oxide, thermoplastic polyester, polyimide, polyphenylene sulfide, polysulfones, aromatic polyamides, polyarylate, polyphenyl ester, polyaryletherketone, a liquid crystal polymer, and fluororesin.

In other embodiments, the thermoplastic polymer may also include materials obtained by organic modification of the above polymers or obtained by inorganic modification by filling the above polymers with an inorganic material. Furthermore, the modification may be chemical or physical modification, or in any other suitable manner.

The organic modification may be for example organosilicon modification, organofluorine modification, graphene modification, silane modification, acrylate copolymerization modification, vinyl monomer modification, aromatic monomer modification and the like, but not limited thereto.

The inorganic modification may be for example heavy calcium modification, talc modification, graphene modification, water glass modification, attapulgite modification, kaolin modification, light calcium modification, glass microbeads modification and the like.

As shown in FIG. 2, the mold 200 comprises a head portion 210 and a tail portion 220. The front end of the head portion 210 comprises a semen pouch 211, which is optional. The rear end of the head portion 210 comprises a transition section 212 for connecting the tail portion 220. The head portion 210 has a length H1 of, for example, 200-260 mm, such as 220 mm, 230 mm or 245 mm, from the view point of molding. The head portion 210 has a columnar shape with a gradually increasing diameter, and has a slope greater than 0° and less than or equal to 5°, such as 2°, 3° or 4°. In particular, the section of the head portion 210 close to the front end may have a diameter of 30-45 mm, and the section of the head portion 210 close to the rear end may have a diameter greater than that of the section close to the front end, for example, 32-50 mm, so that a desired slope is formed by the diameter difference between the two ends. When the mold 200 has a slope within the above range, the mold 200 can be smoothly pulled out of the injection molding machine as described in detail below, so as to further reduce the demolding resistance. The tail portion 220 is connected to the head portion 210 via the transition section 212 to form a smooth surface. The tail portion 220 has a length H2 of, for example, 10-150 mm, such as 25 mm, 30 mm, 35 mm, 40 mm, or 55 mm. The tail portion 220 has a columnar shape with a constant diameter which is consistent with the diameter of the end section of the head portion 210. Certainly, the tail portion may also have a columnar shape with a gradually increasing diameter, and for example has a slope greater than 0° and less than or equal to 3°, for example 1°, 2°, or 3°. The mold 200, when placed vertically, forms an angle less than 5° with respect to the vertical line, thereby sufficiently ensuring that the mold 200 in use, for example when used vertically, has excellent stability and the polyurethane film is not easily damaged because of the rolling and demolding processes.

As shown in FIG. 2, the mold 200 composed of the thermoplastic polymer has a thickness of, for example, 2-25 mm or is a solid mold, and preferably has a thickness of 2-8 mm, for example, 3 mm, 4 mm, 5 mm, 6 mm, 7 mm, etc. The mold 200 may have a reliable strength by having the thickness in the above range.

As shown in FIG. 2, the mold 200 has a surface roughness (Ra) of 0.2 μm or less, such as 0.09 μm, 0.09 μm, 0.05 μm or 0.01 μm. When the surface roughness (Ra) of the mold 200 is 0.2 μm or less, the polyurethane film is easy to handle during demolding without an additional release agent for demolding, and damage to the polyurethane film due to external force is avoided.

As shown in FIG. 3, the present disclosure also provides a method for manufacturing the mold 200, comprising:

Step S1, providing a thermoplastic polymer;

Step S2, injection molding the thermoplastic polymer to produce the mold 200.

The mold 200 may be obtained, for example, by using an injection molding machine. A multi-shot feed, such as a three-shot feed, may be employed to ensure uniform feeding of the thermoplastic polymer in the injection molding machine. Furthermore, the mold 200 may be obtained by two-stage molding, in which the head portion 210 and the tail portion 220 are separately formed and then assembled to form the mold 200, but not limited thereto. The head portion 210 and the tail portion 220 may also be integrally molded.

When the mold 200 is used to mold a polyurethane condom, the mold 200 is hung vertically, dipped in an emulsion of waterborne polyurethane, and then taken out to allow the polyurethane to form a film on its surface, followed by demolding. The polyurethane film can be demolded smoothly without a release agent, and does not adhere to the mold 200.

In a particular embodiment of the present disclosure, the mold 200 can be manufactured by a method comprising three-shot feeding through the open end of the tail portion 210 and two-stage injection molding, wherein polyethylene (Enable™ performance polyethylene from ExxonMobil Chemical) is formed into a cylindrical tubular body for the mold by injection molding. The head portion 210 has a length H1 of 220 mm, and a slope of 0.2° from the front end to the rear end, such that the diameter of the front end of the head portion 210 is smaller than the diameter of the rear end thereof and of the tail portion. The tail portion 220 has a length H2 which is not limited. The mold 200 has a wall thickness of 2 mm, a surface roughness (Ra) of 0.2 μm or less, and a verticality, the angle between the vertically placed mold and the vertical line, less than 5°.

In another particular embodiment of the present disclosure, the mold 200 can be manufactured by a method comprising three-shot feeding through the open end of the tail portion 210 and two-stage injection molding, wherein polypropylene (TB54I from Hanwha-Total) is formed into a cylindrical tubular body for the mold by injection molding. The head portion 210 has a length H1 of 230 mm, and a slope of 3° from the front end to the rear end, such that the diameter of the front end of the head portion 210 is smaller than the diameter of the rear end thereof and of the tail portion. The tail portion 220 has a length H2 which is not limited. The mold 200 has a wall thickness of 5 mm, a surface roughness (Ra) of 0.2 μm or less, and a verticality, the angle between the vertically placed mold 200 and the vertical line, less than 5°.

In another particular embodiment of the present disclosure, the mold 200 can be manufactured by a method comprising three-shot feeding through the open end of the tail portion 210 and two-stage injection molding, wherein polycarbonate (Bayer 2407) is formed into a cylindrical tubular body for the mold by injection molding. The head portion 210 has a length H1 of 240 mm, and a slope of 5° from the front end to the rear end, such that the diameter of the front end of the head portion 210 is smaller than the diameter of the rear end thereof and of the tail portion. The tail portion 220 has a length H2 which is not limited. The mold 200 has a wall thickness of 10 mm, a surface roughness (Ra) of 0.2 μm or less, and a verticality, the angle between the vertically placed mold 200 and the vertical line, less than 5°.

The above description is merely preferred embodiments of the present disclosure, and is not intended to limit the present disclosure. For a person skilled in the art, the features in the above-described embodiments can be combined with each other as long as there is no conflict, and the present disclosure can also have various modifications and changes. Any modifications, equivalents, improvements, etc. that fall within the spirit and principles of the present disclosure are intended to be included within the scope of the present disclosure. Furthermore, the examples are to be construed as illustrative and not restrictive, while the scope of the present disclosure is defined by the appended claims rather than by the foregoing description. All changes which come within the meaning and range of equivalency of the claims are therefore intended to be included herein. Any reference number used in a claim should not be construed as limiting the claim.

What is claimed is:

1. A mold for molding a polyurethane condom, wherein the mold comprises a surface roughness of 0.2 μm or less, wherein the mold is composed of a thermoplastic polymer having a surface tension of 10-35 mN/m, and wherein the thermoplastic polymer is any one selected from polymethyl methacrylate, polystyrene, polyvinyl chloride, polyoxymethylene and materials obtained by organic modification of the above polymers or by inorganic modification by filling the above polymers with an inorganic material, or any combination thereof.

2. The mold for molding a polyurethane condom according to claim 1, wherein the organic modification is selected from the group consisting of organosilicon modification, organofluorine modification, silane modification, acrylate copolymerization modification, vinyl monomer modification, and aromatic monomer modification, and any combination thereof.

3. The mold for molding a polyurethane condom according to claim 1, wherein the inorganic modification is selected from the group consisting of calcium carbonate modification, talc modification, graphene modification, water glass modification, attapulgite modification, kaolin modification, and glass microbeads modification, and any combination thereof.

4. The mold for molding a polyurethane condom according to claim 1, wherein the polyurethane condom is a male condom, and the mold comprises:

a head portion; and a tail portion connected to the head portion;

wherein the head portion has a columnar shape with a gradually increasing diameter, and has a slope greater than 0° and less than or equal to 5°.

5. The mold for molding a polyurethane condom according to claim 4, wherein the head portion has a front end provided with a semen pouch.

6. The mold for molding a polyurethane condom according to claim 4, wherein the head portion has a length of 200-260 mm.

7. The mold for molding a polyurethane condom according to claim 4, wherein the head portion is connected to the tail portion via a transition section.

8. The mold for molding a polyurethane condom according to claim 4, wherein the tail portion has a columnar shape of a constant diameter.

9. The mold for molding a polyurethane condom according to claim 4, wherein the tail portion has a columnar shape with a gradually increasing diameter, and has a slope greater than 0° and less than or equal to 3°.

10. The mold for molding a polyurethane condom according to claim 1, wherein the mold has a thickness of 2-25 mm, or is a solid mold.

11. The mold for molding a polyurethane condom according to claim 1, wherein the mold, when placed vertically, has an angle less than 5° with respect to a vertical axis.

12. A method for manufacturing a mold for molding a polyurethane condom, comprising the steps of:

providing a thermoplastic polymer having a surface tension of 10-35 mN/m; and injection molding the thermoplastic polymer to produce a mold for molding a polyurethane condom;

wherein the mold has a surface roughness of 0.2 μm or less, and wherein the thermoplastic polymer is any one selected from polymethyl methacrylate, polystyrene, polyvinyl chloride, polyoxymethylene and materials obtained by organic modification of the above polymers or by inorganic modification by filling the above polymers with an inorganic material, or any combination thereof.

13. The method for manufacturing a mold for molding a polyurethane condom according to claim 12, wherein the injection molding is carried out by three-shot feed and two-stage injection molding.

14. A method for molding a polyurethane condom, comprising the steps of:

providing a mold;

providing an emulsion comprising a polyurethane resin;

hanging the mold vertically and dipping it in the emulsion containing the polyurethane resin to obtain a dipped mold;

removing the dipped mold and drying it to form a polyurethane film on the surface of the mold; and demolding;

wherein the mold has a surface roughness of 0.2 μm or less, and is composed of a thermoplastic polymer having a surface tension of 10-35 mN/m, and wherein the thermoplastic polymer is any one selected from polymethyl methacrylate, polystyrene, polyvinyl chloride, polyoxymethylene and materials obtained by organic modification of the above polymers or by inorganic modification by filling the above polymers with an inorganic material, or any combination thereof.

15. The method for molding a polyurethane condom according to claim 14, wherein the polyurethane condom has a 100% tensile modulus of 3.5 $N/mm^2$ or lower.

16. The method for molding a polyurethane condom according to claim 14, wherein the polyurethane condom has a burst pressure of 1 kPa or more, a burst volume of 5 L or more, and a 100% modulus of 3.5 $N/mm^2$ or lower.

17. The mold for molding a polyurethane condom according to claim 1, wherein the mold has a surface roughness of 0.09 μm or less.

18. The mold for molding a polyurethane condom according to claim 1, wherein the mold has a surface roughness of 0.05 μm or less.

19. The mold for molding a polyurethane condom according to claim 1, wherein the mold has a surface roughness of 0.01 μm or less.

* * * * *